United States Patent [19]
Biagini et al.

[11] Patent Number: 5,900,517
[45] Date of Patent: May 4, 1999

[54] CYCLOPENTADIENYL DERIVATIVES AND PROCESS FOR THEIR PREPARATION

[75] Inventors: Paolo Biagini, Trecate; Roberto Santi; Giampiero Borsotti, both of Novara; Gabriele Lugli, San Donato Milanese; Viviano Banzi, Vigarano Mainarda, all of Italy

[73] Assignee: Enichem S.p.A., Milan, Italy

[21] Appl. No.: 08/695,400

[22] Filed: Aug. 12, 1996

[30] Foreign Application Priority Data

Aug. 30, 1995 [IT] Italy .................................. MI95A1826
Dec. 21, 1995 [IT] Italy .................................. MI95A2707

[51] Int. Cl.$^6$ ............................ C07C 13/615; C07C 1/32
[52] U.S. Cl. ................................ 585/21; 585/22; 585/357
[58] Field of Search .................................. 585/21, 22, 357

[56] References Cited

PUBLICATIONS

P. 21 of examiner reference "5" of previous Form PTO 892.
Answer 9 of 16, Document No. 103;215140 by Jessen et al Chem Ber., 118(8), 3287–98 (German) 1985 abstract pp. 14, 15.
Answer 12 of 16 Document No. 83:113736 by McAndrew et al. J. Chem Soc., Perkin Trans. 1 (12), 1172–80 (English) 1975 abstract pp. 19,20.
Alfred Pauli, et al., "Tetrahydropentalene", Chemische Berichte, vol. 120, 1987 Weinheim DE, (pp. 1617–1620).
V. A. Mironov, et al., "Cyclic Unsaturated Compounds.XXXVIII. The Thermal Rearrangements of Spiro[4,4] Nona–1,3–Diene [1]", No. 39, 1969 Oxford GB, (pp. 3347–3350).

Gérard Dauphin, et al., "Cyclisation de Systemes Trieniques. V. Peparation d'un Hexahydroazulene", No. 8–9, 1970 Paris FR, (pgs. 3162–3163).

*Primary Examiner*—Jeffrey T. Smith
*Assistant Examiner*—N. Sarofim
*Attorney, Agent, or Firm*—Oblon, Spivak, McClelland, Maier & Neustadt, P.C.

[57] ABSTRACT

Cyclopentadienyl derivatives are described having general formula (I)

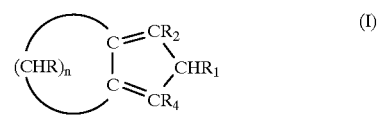

where $R$, $R_1$, $R_2$, $R_4$, equivalent to or different from one another, are selected from: —H, alkyl radicals having a number of carbon atoms from 1 to 5, cycloalkyl radicals having a number of carbon atoms from 5 to 8, aryl and alkylaryl radicals having a number of carbon atoms from 6 to 8, aralkyl radicals having a number of carbon atoms from 7 to 9; n is an integer from 2 to 18; with the proviso that the number of R different from H does not exceed 2; with the exclusion of the compound having $n=3$, $R=R_1=R_2=R_4=H$. The invention a-so describes the process for the preparation of the above-mentioned cyclopentadienyl derivatives.

27 Claims, No Drawings

CYCLOPENTADIENYL DERIVATIVES AND PROCESS FOR THEIR PREPARATION

The present invention relates to new cyclopentadienyl derivatives and the process for their preparation.

It is known that the more useful soluble catalysts for the homo- and co-polymerisation of α-olefins consist of zirconium or titanium complexes bearing ligands of bis-indenyl, bis-fluorenyl type, or mixed fluorenyl cyclopentadienyl type (P. C. Mohring, N. J. Coville, Jr Organomet. Chem. 479, 1, 1994).

It is also known that the corresponding tetrahydroindene derivatives, beside having a high activity, are more effective in the incorporation of co- and ter-monomers and are, therefore, among the preferred catalysts.

The indene or fluorene derivatives are easily available, but the corresponding tertrahydroindenyl derivatives are obtained by direct hydrogenation of the zirconium complex, as it is difficult to chemoselectively hydrogenate the starting ligands.

The hydrogenation process of the complex shows, notwithstanding, some incoveniences. In fact, as is reported by some experts (see E. Samuel, Bull. Soc Chim. Fr., 3548, 1966 and S. Collins et al. in Organometallic Chem., 342, 21, 1988), in effecting said hydrogenation difficulties are found due to low yields and/or drastic conditions.

New cyclopentadienyl derivatives have, now, been found, which overcome the above-mentioned disadvantages, because of their structure, they do not need the above-mentioned hydrogenation step of the complex with the zirconium.

In accordance with this, the present invention relates to cyclopentadienyl derivatives having general formula (I)

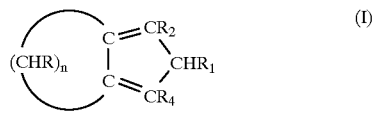

wherein:
$R$, $R_1$, $R_2$, $R_4$, equivalent to or different from one another, are selected from:
H,
alkyl radicals having a number of carbon atoms from 1 to 5,
cycloalkyl radicals having a number of carbon atoms from 5 to 8,
aryl and alkylaryl radicals having a number of carbon atoms from 6 to 8,
aralkyl radicals having a number of carbon atoms from 7 to 9;
n is an integer from 2 to 18;

with the proviso that the number of R different from H does not exceed 2;

with the exclusion of the compound having n=3, $R=R_1=R_2=R_4=H$.

Typical examples of alkyl radicals from C1 to C5 are methyl, ethyl, n-propyl, iso-propyl, n-butyl, iso-butyl, ter-butyl, n-pentyl, iso-pentyl, neo-pentyl.

Typical examples of cycloalkyl radicals having a number of carbon atoms from 5 to 8 are cyclopentyl, cyclohexyl, methyl cyclopentyl, methyl cyclohexyl.

Typical examples of aryl and alkylaryl radicals having a number of carbon atoms from 6 to 8 are phenyl, methyl phenyl, ethyl phenyl, dimethyl phenyl.

Typical examples of aralkyl radicals having a number of carbon atoms from 7 to 9 are benzyl, methyl benzyl, ethyl benzyl, propyl benzyl.

In a preferred form of embodiment, R, $R_1$, $R_2$, and $R_4$ are selected from H and alkyl radicals from C1 to C3.

In an even more preferred form of embodiment, n is selected from 3, 5, 6, 10, $R=R_2=R_1=H$, $R_4$ is selected from H and alkyl radicals from C1 to C3.

Typical examoles of compounds having general formula (I) are:

2,4,5,6,7,8-hexahydroazulene (compound Ia in scheme 1, where $R=R_1=R_2=H$, n=5);

4,5,6,7,8,9-hexahydro-2H-cyclopentacyclooctene (compound Ia in scheme 1, where $R=R_1=R_2=H$, n=6), 4,5,6,7,8,9,10,11,12,13-decahydro-2H-cyclopentacyclododecene (compound Ia in scheme 1, where $R=R_1=R_2=H$, n=10), 1-methyl-4,5,6,7,8,9,10,11,12,13-decahydro-2H-cyclopentacyclododecene (compound Ib in scheme 1, where $R=R_1=R_2=H$, $R_4=CH_3$, n=10).

The compounds having general formula (I) are useful as ligands in the preparation of the complexes with transition metals, Zirconium in particular, typical catalyst components in the (co)polymerisation of α-olefins.

A process for the preparation of chemical compounds having general formula (I) constitutes a further object of the present invention.

This process, schematically represented in scheme 1, where the compounds having general formula (I) are subdivided into (Ia) and (Ib) compounds, whether $R_4$ is equivalent to or different from H, foresees some common steps and a different final step as a function of $R_4$.

The process of the present inventions simple and original, is schematized in Scheme 1.

SCHEME 1

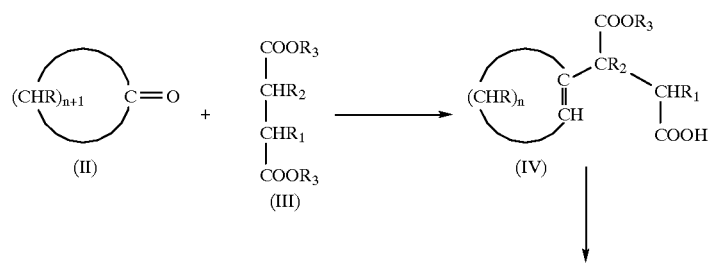

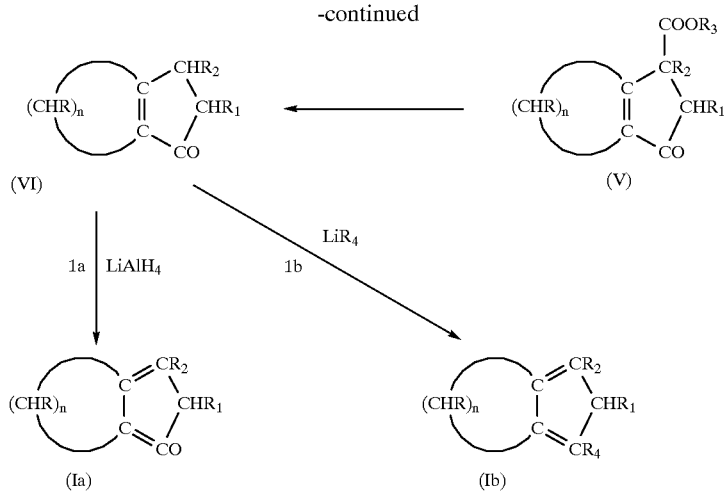

In accordance with this, the present invention relates to a process for the preparation of the compounds having general formula (Ia), where n is an integer from 2 to 18, preferably n is selected from 3, 5, 6, 10, and R, $R_1$, and $R_2$ have the above-mentioned meaning, preferably $R=R_1=R_2=H$, which comprises the following steps:

a) Stobbe type condensation between a ketone having general formula (II)

with an ester of the succinic acid having general formula (III) $R_3OOC—CHR_2—CHR_1—COOR_3$, where the groups $R_3$, equivalent or different from one another, are selected from monofunctional alkyl radicals $C_1–C_5$, preferably $R_3$ is selected from, $CH_3$ and $C_2H_5$ to give the α-(α'-cyclo-alkenyl)-β-hydroxycarbonyl-alkyl propionate having general formula (IV);

b) intramolecular condensation of the compound (IV) obtained in step (a) to give the condensed rings compound having general formula (V);

c) hydrolysis and decarboxylation of the compound (V) obtained in step (b) to give the α-β unsaturated condensed rings ketone having general formula (VI);

d) reduction of the α-β unsaturated condensed rings ketone (VI) obtained in step (c) to give the condensed rings conjugated diene having general formula (Ia), steps (b) and (c) also being able to be carried out in inverted order as compared to the above-mentioned one, or in a single step, preferably in the sequence (a) (b), (c), (d).

Step (a) of the present invention is a typical condensation between ketones and esters of the succinic acid, known as Stobbe reaction.

This reaction (see H. House, Modern Synthetic Reactions, pages 663–666, Organic Reactions, Volume VI, pages 2–58) consists in the condensation of a carbonyl derivative with a diester of the succinic acid.

In case the carbonyl derivative is a cycloalkanone, as in the above-mentoned case, the hemiester of the cyclo alkenyl substituted succinic acid, having general formula (IV) is formed.

Step (a) is carried out in the presence of strong bases, such as sodium methoxide, sodium hydride, tertiary alcohol alcoholates, preferably potassium terbutylate, a typical non-nucleophile strong base. As far as the other experimental details of the Stobbe reaction are concerned, please refer to the above-mentioned references. Typical cyclic ketones having general formula (II) are cyclobutanone, cyclopentanone, cyclohexanone, cycloheptanone, cyclooctanone, cyclododecanone, 2-, 3-, 4-methyl cyclohexanone, phenyl cyclohexanone, benzyl cyclohexanone. One of the advantages of the process of the present invention consists in the fact that many ketones having general formula (II) are commercially available products.

The condensation of step (a) occurs with a diester of the succinic acid having general formula (III), preferably with a diethyl or dimethl succinate, eventually monosubstituted or disubstituted.

Step (b) of the process of the present invention consists in an intramolecular condensation, with the elimination of water, of the product having general formula (IV) obtained in step (a) to give the condensed rings compound having general formula (V).

This step is carried out in the presence of usual condensation agents, for instance, strong acids such as sulphuric acid, hydrofluoric acid, phosphoric acid, polyphosphoric acid, preferably in the presence of polyphosphoric acid. The above-mentioned acid can be used as commercially available or prepared in situ by mixing phosphoric acid and $P_2O_5$.

If polyphosphoric acid is used, it is preferable to carry out step (b) at temperatures between 70 and 110° C.

Alternatively, step (b) can be carried out in the presence of $ZnCl_2$ in acetic acid—acetic anhydride, as is described in the above-mentioned quotation from Organic Reactions.

Step (c) consists in the hydrolysis of the ester group and in the subsequent decarboxylation of the compound having general formula (V) to give the α-β unsaturated condensed rings ketone having general formula (VI). The reaction is preferably carried out in an acid environment and at such temperatures as to facilitate the elimination and the removal of $CO_2$, preferably in a mixture of acetic acid/hydrochloric acid at reflux temperature The α-β unsaturated ketone (VI) formed in step (c) is then reduced (step d) to a cyclopentadienyl derivative having general formula (Ia) in the presence of reducing agents such as sodium or lithium boron hydride, sodium hydride, lithium hydride, lithium aluminium hydride, preferably with $LiAlH_4$.

According to another form of embodiment of the process of the present invention, step (c), i.e. the hydrolysis to carboxylic acid and the subsequent decarboxylation, can be carried out before the step of intramolecular condensation (b), or the two steps can be carried out in a single step by selecting the most appropriate reaction conditions.

The process of the present invention does not necessarily require the isolation of the single reaction products at the end of the single steps.

Beside the advantage to start from easily available cycloakanones, the process foresees rather simple chemical steps and has a satisfactory global yield.

The present invention also relates to a process for the preparation of the compounds having general formula (Ib), where n is an integer from 2 to 18, preferably selected from 3, 5, 6, 10, R, $R_1$, $R_2$, $R_4$ have the above-mentioned meaning but with the proviso that $R_4$ is different from H, preferably $R=R_1=R_2=H$, which comprises the following steps:

a) Stobbe type condensation between a ketone having general formula (II)

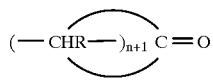

with an ester of the succinic acid having formula (III) $R_3OOC-CHR_2-CHR_1-COOR_3$, where the groups $R_3$, equivalent or different from one another, are selected from monofunctional alkyl radicals $C_1-C_5$, preferably $R_3$ is selected from $CH_3$ and $C_2H_5$, to give the α-(α'-cyclo-alkenyl)-β-hydroxycarbonyl-alkyl propionate having general formula (IV);

b) intramolecular condensation of the compound (IV) obtained in step (a) to give the condensed rings compound having general formula (V);

c) hydrolysis and decarboxylation of the compound (V) obtained in step (b) to give the α-β unsaturated condensed rings ketone having general formula (VI);

d) reaction of the α-β unsaturated condensed rings ketone (VI) obtained in step (c) with an alkyl, aralkyl, alkylaryl, cycloalkyl derivative of an alkali metal and subsequent hydrolysation to give the condensed rings conjugated diene having general formula (Ib), steps (b) and (c) being also able to be carried out in inverted order as compared to the above-mentioned one, or in a single step, preferably in the sequence (a), (b) (c), (d).

As far as steps (a) to (c) are concerned, they are carried out under the same conditions as the above-mentioned ones for the synthesis of (Ia) compounds Step (d) is carried out by reacting the α-β unsaturated condensed rings ketone (VI) obtained in step (c) with an alkyl, aralkyl, alkylaryl, cycloalkyl derivative of an alkali metal, preferably lithium The hydrocarbon derivative of lithium is a function of the type of $R_4$ that one is willing to introduce in the compound having general formula (Ib). So, for instance, in case one is willing to prepare an (Ib) compound where $R_4$ is equivalent to—$CH_3$, one will use methyl lithium; in case one is willing to prepare an (Ib) compound where $R_4$ is equivalent to —$C_2H_5$, one will use ethyl lithium.

Step (d) then foresees a subsequent hydrolysis step, preferably carried out in the presence of acid catalysis, and then a dehydration step, preferably carried out in the presence of acid catalysis, too. The product (Ib) thus obtained can be isolated according to usual techniques.

The following examples are reported for a better illustration of the present invention.

EXAMPLE 1
Synthesis of 2,4,5,6,7,8-hexahydro-azulene (compound of scheme 1 where $R=R_1=R_2=H$, n=5).

To a solution of cycloheptanone, compound (II) where n-=5, (56 grams corresponding to 0.5 moles) and of diethyl succinate, compound (III) where both $R_3$s are equal to —$C_2H_5$, 110 grams (0.63 moles) in 500 ml N,N dimethyl formamide (DMF), potassium terbutylate (75 grams, 0.67 moles) is slowly added (in about 1 hour), maintaining the temperature between 20 and 30° C. At the end a yellow suspension is obtained which, after about one hour is dissolved again to give, then, a complete solidification of the reaction product. It is all poured in about 2 liters water, thus obtaining a limpid solution.

The solution is extracted for some times with ethyl ether and the aqueous solution is then acidified to a pH of 2–3, by using dilute HCl.

The aqueous solution thus acidized is then extracted with ether and the organic extract, after washing with water to neutrality and after drying, is evaporated. 118 grams (99% yield) α-(α'-cycloheptenyl)-β-hydroxycarbonyl-ethyl propionate (compound IV) are obtained pure at the NMR analysis.

The emiester (IV) is then added to a mixture consisting of 400 grams $H_3PO_4$ 85% and 650 grams $P_2O_5$, maintaining the temperature between 90 and 92° C.

Once the addition has ended, the temperature is maintained for further 4 hours, during which there is an abundant development of foam.

The mixture is then hydrolized with water and extracted with diethyl ether. The ethereal extract is neutralized and dried. After the evaporation of the solvent, 35 grams of raw residue (64% yield of product V) are obtained, which are poured into 100 ml AcOH, 100 ml water and 10 ml concentrated HCl and then maintained at reflux temperature for one night. The reaction mass is diluted with water and extracted with petroleum ether. After the neutralization, drying and evaporation of the solvent, 16 grams 3,4,5,6,7, 8-hexahydro-2H-azulen-1-one (64% yield of product VI) are obtained.

16 grams of product (VI) dissolved in 200 ml diethyl ether are added to a solution of 3.0 grams of $LiAlH_4$ in 300 ml diethyl ether, maintaining the temperature between 5 and 10° C. The reaction mixture is then hydrolized, the ethereal layer separated and the aqueous step extracted, again with 200 ml diethyl ether.

The ethereal extracts, (800 ml) after neutralisation and anhydrification are treated with 1.0 grams p-toluenesulphonic acid for 1.5 hours at room temperature. The organic phase is then neutralized with $NaHCO_3$ and evaporated. The residue obtained is purified by chromatography on a silica gel column by eluting it with petroleum ether.

14 grams of 2,4,5,6,7,8-hexahydroazulene, (compound Ia with n=5) are obtained with a yield of 98% from the product (VI) and of 40% from the starting cycloheptanone, which has the following NMR spectrum: $^1$H-NMR (CDCl$_3$, δ ppm rel. TMS): 5.96 (s, br, 2H); 2.84 (t, 2H, J=2Hz); 2.47 (m, 4H); 1.61 (m, 6H).

EXAMPLE 2
Synthesis of 4,5,6,7,8,9-hexahydro-2H-cyclopentacyclooctene (compound Ia of scheme 1 where $R=R_1=R_2=H$, n=6).

A solution of 63 grams (0.5 moles) of cyclooctanone (II) and 110 grams (0.63) moles diethyl succinate is prepared.

75 grams (0.67 moles) Potassium terbutylate are added to this solution in small portions.

After the addition, the mixture is left under stirring for 4 hours. The orange mass is hydrolized with water and ice, one acidizes and one extracts with diethyl ether. 140 grams of a raw semi-solid containing two products in a ratio 84:16 are obtained upon evaporation.

70 grams of the raw ester thus prepared are added to the polyphosphoric acid (consisting of 300 grams 85% $H_3PO_4$ and 450 grams $P_2O_5$). Exothermic reaction takes place and at 70° C. the ester goes into a solution, the mass browns and the temperature goes up to 92° C. The reaction mass is stirred for about ½ hour. Tie temperature goes down to 80° C. The reaction mixture is pored into ice, is extractd with diethyl ether, neutralized with an aqueous solution of $NaHCO_3$, anhydrified and the solvent evaporated. 35 grams brown oil are obtained.

A mixture is prepared containing the 35 grams of the above-mentoned raw oil, 100 ml AcOH, 100 ml water and 10 ml concentrated HCl.

This mixture is maintained at reflux temperature for 6 hours, at the end of which is hydrolized and extractd with diethyl ether. Many pitches separate. The mixture is washed with NaOH (pitches dissolve) and water, anhydrified and the solvent evaporated. 12 grams yellow oil are obtained.

These 12 grams yellow oil (corresponding to product VI), dissolved in 100 ml diethy ether, are added to a solution of 3.0 grams $LiAlH_4$ in 200 ml diethyl ether, maintaining the temperature between 5 and 10° C.

The reaction mixture is then hydrolized, the ethereal layer separated and the aqueous step extracted, still with 100 ml diethyl ether.

The ether extracts (400 ml), after neutralisation and anhydrification, are treated with 1.0 grams p-toluenesulphonic acid for 1.5 hours at room temperature. The organic phase is then neutralized with $NaHCO_3$ and evaporated. The residue obtained is purified by chromatography on a silica gel column by eluting with petroleum ether.

7 grams of (Ia) product, pure at the NMR and GC analysis, are obtained.

The yield, as compared to the starting cyclooctanone (II), is of 20%.

The NMR spectrum of the 4,5,6,7,8,9-hexahydro-2H-cyclopentacyclooctene thus obtained is the following:

$^1$H-NMR (CDCl$_3$, δ ppm rel. TMS): 6.02 (t, 2H); 2.88 (bs, 2H); 2.50 (t, 4H); 1.70–1.40 (m, 8H).

EXAMPLE 3

Synthesis of 4,5,6,7,8,9,10,11,12,13-decahydro-2H-cyclopentacyclododecene (compound Ia of scheme 1 where $R=R_1=R_2=H$, n=10).

To a solution of 100 grams (0.549 moles) cyclododecanone (compound II, n=10) in 700 ml THF, 70 grams Potassium terbutylate are slowly added about 1 hour). At the end, a yellow suspension is obtained which is agitated for 1 hour. The whole is poured in about 2 liters water, thus obtaining a limpid solution.

The aqueosus solution is washed for some times with diethyl ether and then acidicified to a pH of 2–3, by using diluted HCl.

The aqueous solution is then extracted with ether and the organic extract, after washing with water to neutrality and after drying, is evaporated.

160 grams (94% yield) of a product having a low melting point (product IV in scheme 1 where n=10, $R=R_1=R_2=H$, $R_3=Et$) are obtained.

The ester thus obtained (120 grams, 0.387 moles) is poured in one hour into a flask, maintained at about 93–95° C., containing 2.5 Kg polyphosphoric acid having a $P_2O_5$ content of 84%. Once the addition has ended, the temperature is raised to 96–97° C. and the mixture left under stirring for 4 hours.

The mixture is then hydrolized with water and extracted with diethyl ether. The ether extract is neutralized and dried. After the evaporation of the solvent, 90 grams of a raw residue, pure at the GC analysis (product V in scheme 1, where n=10, $R=R_1=R_2=H$, $R_3=Et$) are obtained.

The solid is put into a solution consisting in 125 ml AcOH, 125 ml water and 10 ml concentrated HCl, and maintained under reflux temperature for 20 hours. The reaction mass is diluted with water and extracted with petroleum ether. After the neutralization, drying and evaporation of the solvent, the residue is distilled under vacuum and the fraction which passes at 125–130° C./0.2 mmHg is collected. 43 grams (51% yield) of product VI in scheme 1 having n=10, $R=R_1=R_2=H$, are obtained.

24 grams (0.11 moles) of the product thus obtained are dissolved in 200 ml diethyl ether and then added to a solution of 3.0 grams $LiAlH_4$ in 300 ml diethyl ether, maintaining the temperature between 5 and 10° C.

The reaction mixture is then hydrolized with some diluted HCl, the ethereal layer separated and the aqueous phase extracted still with 200 ml diethyl ether.

The ethereal extracts, (800 ml) after neutralisation and anhydrification are treated with 2.7 grams p-toluenesulphonic acid for 1.5 hours at room temperature, then at 30–35° C. for 5–6 hours until the alcohol (TLC) has disappeared. The organic phase is then neutralized with $NaHCO_3$ and evaporated. The residue obtained is purified by chromatography on a silica gel column by eluting with petroleum ether.

21 grams (99% yield) of a mixture consisting in two products in a ratio of 81:19, of which the main product is 4,5,6,7,8,9,10,11,12,13-decahydro-2H-cyclopentacyclododecene (compound Ia in scheme 1, n=10, $R=R_1=R_2=H$) are obtained.

EXAMPLE 4

Synthesis of 1-methyl-4,5,6,7,8,9,10,11,12,13-decahydro-2H-cyclopentacyclododecene (compound Ib in scheme 1, where $R=R_1=R_2=H$, $R_4=CH_3$, n=10).

To a solution, In 100 ml diethyl ether, of 10 grams (0.045 moles) of the carbonylic derivative prepared in example 3 (product VI in scheme 1, n=10, $R=R_1=R_2=H$), maintained at −70° C., 30 ml of a solution 1.6M of MeLi in diethyl ether are added. The mixture is left under stirring for one night, then hydrolyzed. The ethereal phase is separated, 1 gram p-toluenesulphonic acid is added and the mixture is left under stirring for 2 hours.

The mixture is neutralized with a saturated solution of sodium bicarbonate, dried on $Na_2SO_4$ and the solvent is evaporated. The product is eluted on a silica gel column by using petroleum ether and by collecting the first fraction. 7 grams of a product consisting in two isomers in a ratio of 3:1 from the gaschromatographic analysis are obtained.

The main product of the above-mentioned mixture is consisting in 1-methyl-4,5,6,7,8,9,10,11,12,13-decahydro-2H-cyclopentacyclododecene.

We claim:

1. A process for the preparation of the compounds having formula (Ia):

$$(CHR)_n \begin{array}{c} C=CR_2 \\ | \\ C=CH \end{array} CHR_1 \qquad (Ia)$$

where n is an integer from 2 to 18, R, $R_1$ and $R_2$ have the above-mention meaning, which comprises the following steps:

a) Stobbe type condensation between a ketone having formula (II)

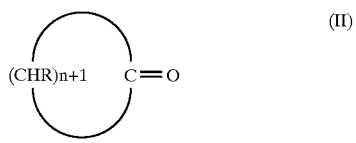

with an ester of the succinic acid having formula (III)

where thy groups $R_3$, equivalent to or different from one another, are selected from monofunctional alkyl radicals $C_1-C_5$ to give the $\alpha$-($\alpha'$-cycloalkenyl)-$\beta$-hydroxycarbonylalkyl propionate having formula (IV):

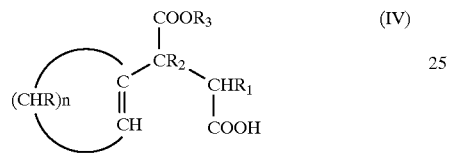

b) intramolecular condensation of the compound (IV) obtained in step (a) to give the condensed rings compound having formula (V):

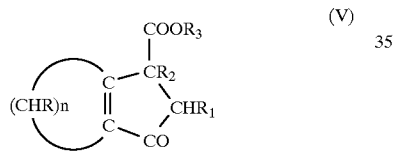

c) hydrolysis and decarboxylation of the compound (V) obtained in stop (b) to give the $\alpha,\beta$-unsaturated condensed ring ketone having formula (VI):

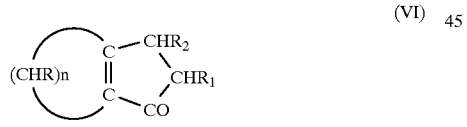

d) reduction of the $\alpha,\beta$-unsaturated condensed rings ketone (VI) obtained in step (c) to give the conjugated condensed ring diene having formula (Ia) steps (b) and (c) also being able to be carried out in the inverted order as compared to the above-mentioned one, or in a single step.

2. Process according to claim 1, characterised by the fact that $R_3$ is selected from —$CH_3$ and —$C_2H_5$.

3. Process according to claim 1, where $R=R_1=R_2=H$.

4. Process according to claim 1, where n is selected from 3, 5, 6, 10.

5. Process according to claim 1, characterised by the fact that step (a) is carried out in the presence of Potassium terbutylate.

6. Process according to claims 1, characterised by the fact that step (b) is carried out in the presence of polyphosphoric acid as such or prepared in situ.

7. Process according to claim 1, characterised by the fact that step (c) is carried out at acid pHs.

8. Process according to claim 1, characterised by the fact that step (d) is carried out in the presence of $LiAlH_4$.

9. Process according to claim 1, characterised by the fact that it is carried out in the following step sequence: step (a), step (b), step (c), step (d).

10. A process for the preparation of the compounds having formula (Ib):

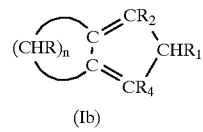

where n is an integer from 2 to 18, R, $R_1$, $R_2$, $R_4$ have the above-mentioned meaning but with the proviso that $R_4$ is different from H, which comprises the following steps:

a) Stobbe type condensation between a ketone having formula (II):

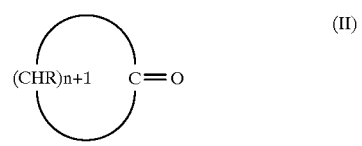

with an eater of the succinic acid having formula (III)

where the groups $R_3$, equivalent or different from one another, are selected from monofunctional alkyl radicals $C_1-C_5$, to give the $\alpha$-($\alpha'$-cycloalkenyl)-$\beta$-hydroxycarbonyl-alkyl propionate having formula (IV):

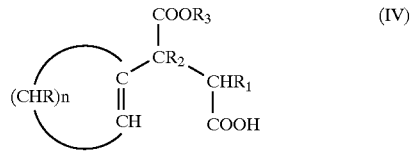

b) intramolecular condensation of the compound (IV) obtained in step (a) to give the condensed ring compound having formula (v):

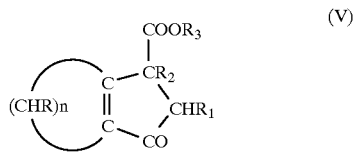

c) hydrolysis and decarboxylation of the compound (V) obtained in step (b) to give the $\alpha,\beta$-unsaturated condensed ring ketone having formula (VI):

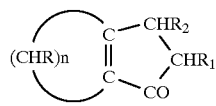

(VI)

d) reaction of the α,β-unsaturated condensed ring ketone (VI) obtained in step (c) with an alkyl, aralkyl, alkylaryl, cycloalkyl derivative of an alkali metal and subsequent hydrolyzation to give the conjugated condensed ring diene having formula (Ib), steps (b) and (c) also being able to be carried out in the inverted order as compared to the above-mentioned one, or in a single step.

11. Process according to claim 10, characterised by the fact that R3 is selected from—$CH_3$ and —$C_2H_5$.

12. Process according to claim 10, where $R=R_1=R_2=H$.

13. Process according to claim 10, where n is selected from 3, 5, 6, 10.

14. Process according to claim 10, characterised by the fact that step (a) is carried out in the presence of Potassium terbutylate.

15. Process according to claim 10, characterised by the fact that step (b) is carried out in the presence of polyphosphoric acid as it is or prepared in situ.

16. Process according to claim 10, characterised by the fact that step (c) is carried out at acid pHs.

17. Process according to claim 10, characterised by the fact that in step (d) the alkali metal is Lithium and the hydrolysis is carried out with acid catalysis.

18. Process according to claim 1, characterised by the fact that it is carried out in the following step sequence step (a), step (b), step (c), step (d).

19. Cyclopentadienyl derivatives having formula (I)

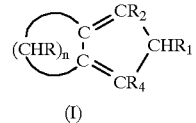

(I)

where R, $R_1$, $R_2$, $R_4$, are the same as or different from one another and are selected from the group consisting of (i) hydrogen, (ii) alkyl radicals having from 1 to 5 carbon atoms, (iii) cycloalkyl radicals having from 5 to 8 carbon atoms, (iv) aryl and alkylaryl radicals having from 6 to 8 carbon atoms, and (v) aralkyl radicals having from 7 to 9 carbon atoms;

n is an integer from 2 to 18;

with the proviso that the number of R groups different from H does not exceed 2;

with the exclusion of the compounds (i) wherein n=3 or 4 and $R=R_1=R_2=R_4=H$.

20. The cyclopentadienyl derivative according to claim 19, where R, $R_1$, $R_2$, $R_4$, are selected from the group consisting of hydrogen and $C_{1-3}$ alkyl groups.

21. The cyclopentadienyl derivative according to claim 19, where n is selected from the group consisting of from 3, 5, 6 and 10, $R=R_2=R_1=H$, and $R_4$ is selected from the group consisting of hydrogen and $C_{1-3}$ alkyl groups, with the proviso that when n=3 or 10, $R=R_2=R_1=R_4$ cannot be hydrogen and that when n=10 and R and $R_1$=hydrogen, neither $R_2$ nor $R_4$ can be methyl while the other is hydrogen.

22. 2,4,5,6,7,8-Hexahydroazulene.

23. 4,5,6,7,8,9-Hexahydro-2H-cyclopentacyclooctene.

24. 4,5,6,7,8,9,10,11,12,13-Decahydro-2H-cyclopentacyclododecene.

25. 1-Methyl-4,5,6,7,8,9,10,11,12,13-decahydro-2H-cyclopentacyclododecene.

26. The process of claim 1, wherein the $R=R_1=R_2=H$ and wherein $R_3$ is methyl or ethyl.

27. The process of claim 10, wherein the $R=R_1=R_2=H$ and wherein $R_3$ is methyl or ethyl.

* * * * *